United States Patent
Yan et al.

(10) Patent No.: US 11,903,565 B2
(45) Date of Patent: Feb. 20, 2024

(54) FLEXIBLE CATHETER-BASED IN VIVO DETECTION DEVICE AND SYSTEM

(71) Applicant: INNOVEX MEDICAL CO., LTD, Shanghai (CN)

(72) Inventors: Hang Yan, Shanghai (CN); Wei Tang, Shanghai (CN); Ruifeng Gao, Shanghai (CN); Zimei Zhang, Shanghai (CN)

(73) Assignee: INNOVEX MEDICAL CO., LTD, Shanghai (CN)

( * ) Notice: Subject to any disclaimer, the term of this patent is extended or adjusted under 35 U.S.C. 154(b) by 533 days.

(21) Appl. No.: 17/049,954

(22) PCT Filed: Jan. 29, 2019

(86) PCT No.: PCT/CN2019/073615
§ 371 (c)(1),
(2) Date: Oct. 22, 2020

(87) PCT Pub. No.: WO2020/113808
PCT Pub. Date: Nov. 6, 2020

(65) Prior Publication Data
US 2021/0235978 A1    Aug. 5, 2021

(30) Foreign Application Priority Data
Jul. 12, 2018   (CN) .......................... 201811495228.7

(51) Int. Cl.
*A61B 1/05*   (2006.01)
*A61B 1/00*   (2006.01)
(Continued)

(52) U.S. Cl.
CPC ............ *A61B 1/051* (2013.01); *A61B 1/0011* (2013.01); *A61B 1/00124* (2013.01);
(Continued)

(58) Field of Classification Search
CPC ... A61B 1/051; A61B 1/0011; A61B 1/00124; A61B 1/018; A61B 1/0676; A61B 1/07;
(Continued)

(56) References Cited

U.S. PATENT DOCUMENTS

2016/0029879 A1   2/2016   Ishikawa

FOREIGN PATENT DOCUMENTS

| CN | 102641124 | 8/2012 |
|----|-----------|--------|
| CN | 102727163 | 10/2012 |

(Continued)

OTHER PUBLICATIONS

PCT/CN2019/073615 International Search Report dated Jun. 11, 2020 and English translation.

*Primary Examiner* — Abdullah A Riyami
*Assistant Examiner* — Justin M Kratt
(74) *Attorney, Agent, or Firm* — NZ Carr Law Office

(57) ABSTRACT

The present invention provides an in-vivo detection apparatus and system based on a flexible tube. The apparatus includes: a detection component, a main circuit board, a detection circuit board, an auxiliary circuit board, a cable, and an outer tube. The in-vivo detection apparatus has improved welding strength and reliability particularly when a packaging size is limited.

27 Claims, 4 Drawing Sheets

(51) Int. Cl.
*A61B 1/06* (2006.01)
*A61B 1/07* (2006.01)
*A61B 1/018* (2006.01)
*A61B 1/005* (2006.01)
*H01R 12/52* (2011.01)
*H01R 12/53* (2011.01)
*H05K 1/18* (2006.01)

(52) U.S. Cl.
CPC ............ *A61B 1/018* (2013.01); *A61B 1/0676* (2013.01); *A61B 1/07* (2013.01); *A61B 1/005* (2013.01); *A61B 1/00114* (2013.01); *A61B 1/00119* (2013.01); *A61B 1/06* (2013.01); *H01R 12/52* (2013.01); *H01R 12/53* (2013.01); *H05K 1/18* (2013.01); *H05K 1/181* (2013.01); *H05K 1/182* (2013.01); *H05K 1/183* (2013.01); *H05K 2201/09027* (2013.01); *H05K 2201/09036* (2013.01); *H05K 2201/10106* (2013.01); *H05K 2201/10151* (2013.01)

(58) Field of Classification Search
CPC . A61B 1/00114; A61B 1/00119; A61B 1/005; A61B 1/06; H01R 12/52; H01R 12/53; H05K 1/18; H05K 1/181; H05K 1/182; H05K 1/183; H05K 2201/09027; H05K 2201/09036; H05K 2201/10106; H05K 2201/10151

See application file for complete search history.

(56) References Cited

FOREIGN PATENT DOCUMENTS

| | | | |
|---|---|---|---|
| CN | 103300809 | 9/2013 | |
| CN | 105636499 | 6/2016 | |
| CN | 107431782 | 12/2017 | |
| WO | WO-2015002847 A2 * | 1/2015 | ........... A61B 1/0005 |

* cited by examiner

FLEXIBLE CATHETER-BASED IN VIVO DETECTION DEVICE AND SYSTEM

TECHNICAL FIELD

The present invention relates to the medical field, and in particular, to an in-vivo detection apparatus and system based on a flexible tube.

BACKGROUND ART

With development of science and technologies, in-vivo detection technologies based on flexible tubes have been widely applied to the medical field. An in-vivo detection apparatus based on a flexible tube can be extended into a human body to help medical personnel inspect an internal organ of the human body.

In the related art, the in-vivo detection apparatus based on the flexible tube may include a flexible controllable curved tube and a detection component disposed at an end of the controllable curved tube. A wiring terminal of the detection component may be welded to another cable through welding, so as to implement electrical transmission.

However, due to a relatively small size of the detection component and a relatively small size of a cable of the detection component, it is inconvenient to weld the detection component to another cable. In addition, it is difficult to ensure a welding effect during motion. For example, it is easy for the cable of the detection component to disconnect from another cable during motion.

SUMMARY

The present invention provides an in-vivo detection apparatus and system based on a flexible tube, to resolve problems that the detection component is inconvenient to operate during welding when a packaging size is limited, and it is difficult to ensure a welding effect during motion.

According to a first aspect of the present invention, an in-vivo detection apparatus based on a flexible tube is provided, including: a detection component, a main circuit board, a detection circuit board, an auxiliary circuit board, a cable, and an outer tube, where the main circuit board is provided with two first edges parallel to each other disposed along a first direction, and a second edge disposed along a second direction;

a first conducting material is disposed on a first side surface of the detection circuit board, the detection component is connected to the first side surface of the detection circuit board, a wiring terminal of the detection component is welded to the first conducting material, a second conducting material is disposed on a second side surface of the detection circuit board, the second side surface of the detection circuit board is connected to the second edge of the main circuit board, the second conducting material is perpendicularly welded to a conductive portion on a surface of the main circuit board, and the conductive portion is conductively connected to the cable; the first conducting material is conducted to the second conducting material;

each auxiliary circuit board is connected to one of the first edges, a channel for at least a part of an instrument tube to pass through is formed between two auxiliary circuit boards, and the channel is provided on a side, along a third direction, of the detection component, the main circuit board, and the detection circuit board;

the detection component, the main circuit board, the detection circuit board, the auxiliary circuit boards, and the part of the instrument tube disposed in the channel are all disposed in the outer tube; the outer tube is directly or indirectly connected to a flexible controllable curved tube; and the first direction, the second direction, and the third direction are perpendicular to each other.

Optionally, the detection component is an image acquisition component.

Optionally, the apparatus further includes a lighting component, where the lighting component is disposed at an end of the auxiliary circuit board, and the lighting component and the detection component face a same direction.

Optionally, a light conducting material is disposed on each of opposite side surfaces of the two auxiliary circuit boards, the light conducting material is welded to a wiring terminal of the lighting component, and two lighting components are connected in parallel by using two light conducting materials.

Optionally, a bayonet is provided along the first direction at an end of the auxiliary circuit board, and the lighting component is disposed at the bayonet.

Optionally, a distance between the lighting component and the first side surface of the detection circuit board along the first direction matches a length of the detection component along the first direction.

Optionally, a surface size of the second conducting material is greater than a surface size of the first conducting material.

Optionally, the detection circuit board and the main circuit board, and/or the auxiliary circuit board and the main circuit board are separately located and connected by using a locating bayonet structure.

Optionally, the cable conductively connected to the conductive portion is a coaxial cable with a shielding layer.

Optionally, the outer tube is filled with glue.

According to a second aspect of the present invention, an in-vivo detection system based on a flexible tube is provided, including the in-vivo detection apparatus based on the flexible tube, the flexible controllable curved tube, and the instrument tube in the first aspect and the optional solutions of the first aspect, where the in-vivo detection apparatus and the instrument tube form an insertion portion at an end of the controllable curved tube.

For the in-vivo detection apparatus and system based on the flexible tube provided in the present invention, the first conducting material is disposed on the first side surface of the detection circuit board, and when the detection component is connected to the first side surface of the detection circuit board, the wiring terminal of the detection component is welded to the first conducting material, so that the wiring terminal of the detection component can be prevented from being welded to the cable. Because the wiring terminal needs to be welded only to the first conducting material on the first side surface, difficulty of welding operations is reduced, welding strength and reliability are enhanced, and welding stability in a plurality of motion statuses is satisfied.

Based on the present invention, stable mounting and use of the detection component are further ensured by using the main circuit board, the detection circuit board, and the auxiliary circuit board, so that the detection component is not impacted by external force. In addition, the side surface of the auxiliary circuit board is connected to the first edge of the main circuit board, the side surface of the detection circuit board is connected to the second edge of the main circuit board, and the channel is formed to provide a cavity structure whose shape is similar to H, thereby helping reduce an overall size of the apparatus by rationalizing space utilization.

In an optional solution of the present invention, because a surface size of the second conducting material is greater than a surface size of the first conducting material, after the main circuit board is perpendicularly welded to the second conducting material of the detection circuit board, a connection between the detection component and the cable may be changed from a point to a line, thereby effectively enhancing welding strength and reliability, and satisfying welding stability in a plurality of motion statuses.

In an optional solution of the present invention, mounting of the lighting component and electrical transmission may be further implemented by using the auxiliary circuit board and the light conducting material on the auxiliary circuit board. In addition, stability of electrical transmission of the lighting component may be further ensured, and size simplification is facilitated.

In an optional solution of the present invention, a distance between the lighting component and the first side surface of the detection circuit board along the first direction matches a length of the detection component along the first direction, so that an end of the lighting component stays in a same plane as an end of the detection component, thereby ensuring lighting uniformity.

BRIEF DESCRIPTION OF THE DRAWINGS

To describe the technical solutions in the embodiments of the present invention or in the prior art more clearly, accompanying drawings required to describe the embodiments or the prior art are briefly described below. It is obvious that the accompanying drawings described below are only some embodiments of the present invention. It is apparent to those of ordinary skill in the art that other drawings may be further obtained based on the accompanying drawings without inventive effort.

DESCRIPTION OF REFERENCE SIGNS

1—detection component;
2—detection circuit board;
21—first conducting material;
22—second conducting material;
23—first extension portion;
3—main circuit board;
31—second extension portion;
32—first bayonet;
33—third extension portion;
4—auxiliary circuit board;
41—light conducting material;
42—second bayonet;
43—third bayonet;
5—lighting component; and
6—instrument tube;
7—outer tube; and
8—support structure.

DETAILED DESCRIPTION

Technical solutions in the embodiments of the present invention are clearly and completely described below with reference to accompanying drawings in the embodiments of the present invention. Apparently, the described embodiments are only some rather than all of the embodiments of the present invention. Based on the embodiments of the present invention, all other embodiments obtained by those of ordinary skill in the art without creative efforts shall fall within the protection scope of the present invention.

Terms "first", "second", "third", "fourth", and the like (if any) in the specification and claims of the present invention and the foregoing accompanying drawings are used to distinguish similar objects, but do not need to be used for describing a specific sequence or an order. It should be understood that data used in this way can be interchanged under appropriate circumstances, so that the embodiments of the present invention described herein can be implemented in an order other than those illustrated or described herein. In addition, terms "including", "having", and any variations thereof are intended to cover non-exclusive inclusions, for example, processes, methods, systems, products, or devices that contain a series of steps or units need not be limited to those clearly listed steps or units, but may include other steps or units not explicitly listed or inherent to these processes, methods, products, or devices.

The technical solutions of the present invention are described in detail below with reference to the specific embodiments. The following several embodiments may be combined with each other, and a same or similar concept or process may not be described again in some embodiments.

Figure 1:
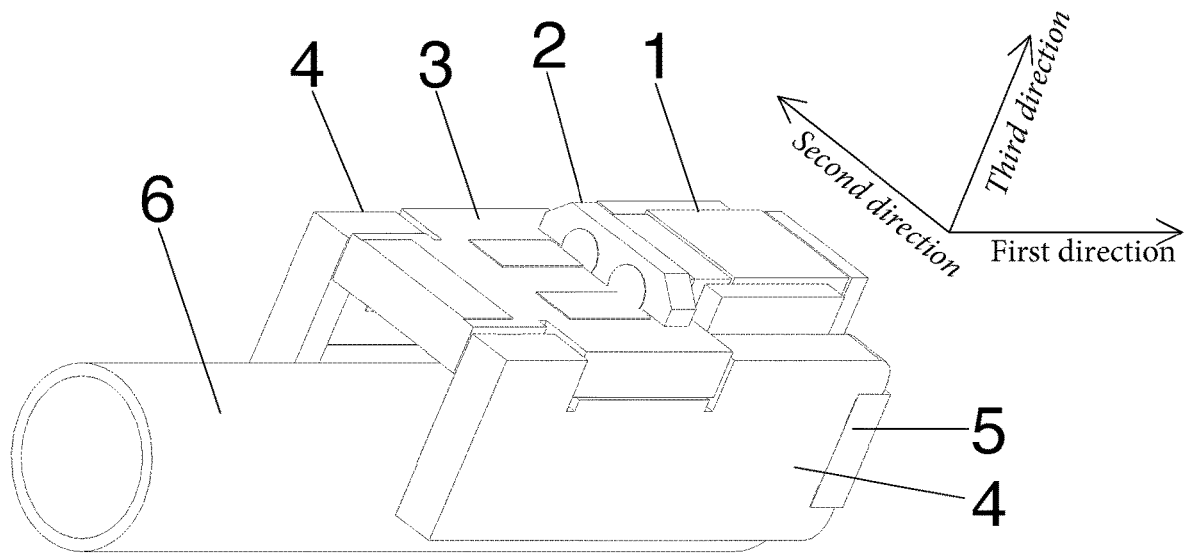
FIG. 1 is a schematic structural diagram 1 of an in-vivo detection apparatus based on a flexible tube according to an embodiment of the present invention.
Figure 2:
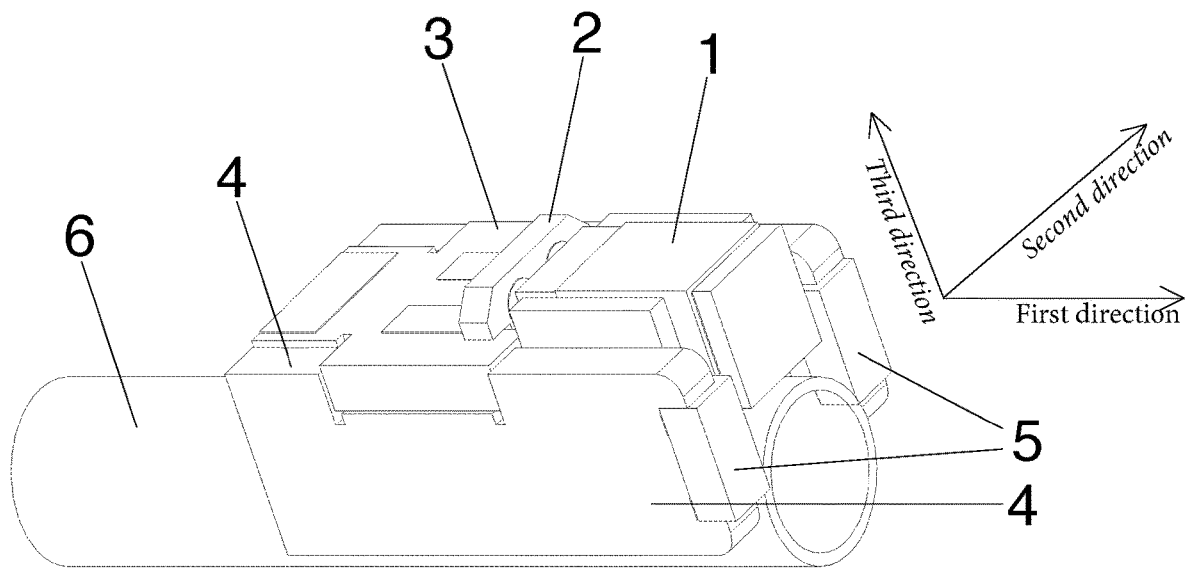
FIG. 2 is a schematic structural diagram 2 of an in-vivo detection apparatus based on a flexible tube according to an embodiment of the present invention.
Figure 3:
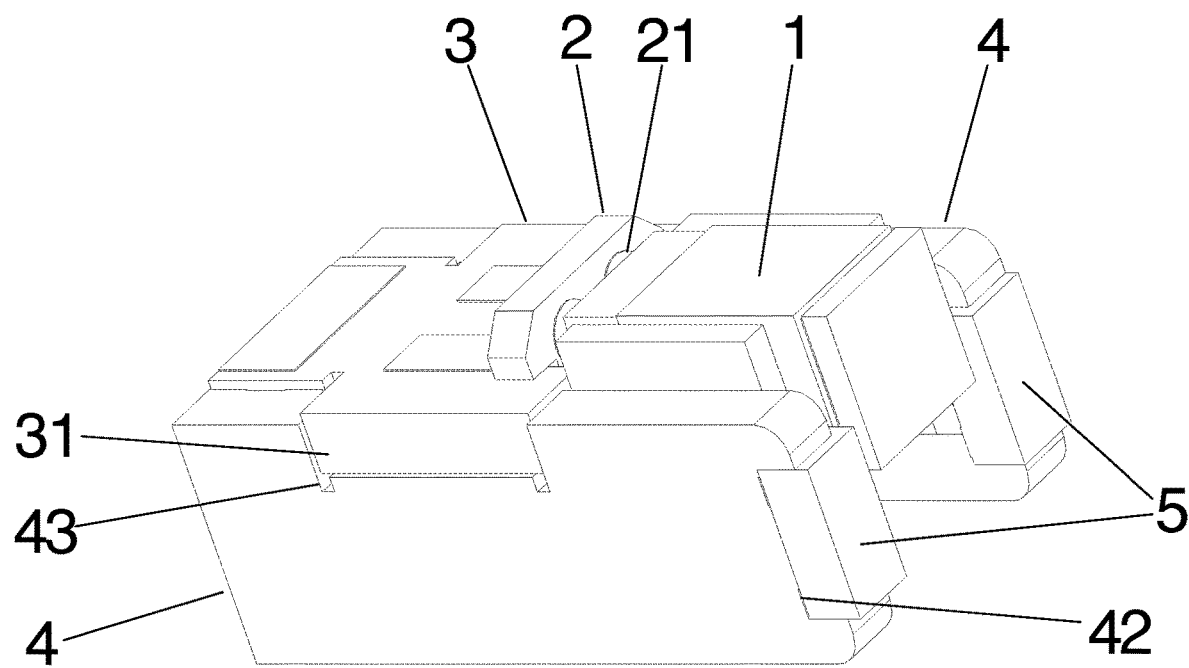
FIG. 3 is a schematic structural diagram 3 of an in-vivo detection apparatus based on a flexible tube according to an embodiment of the present invention.
Figure 4:
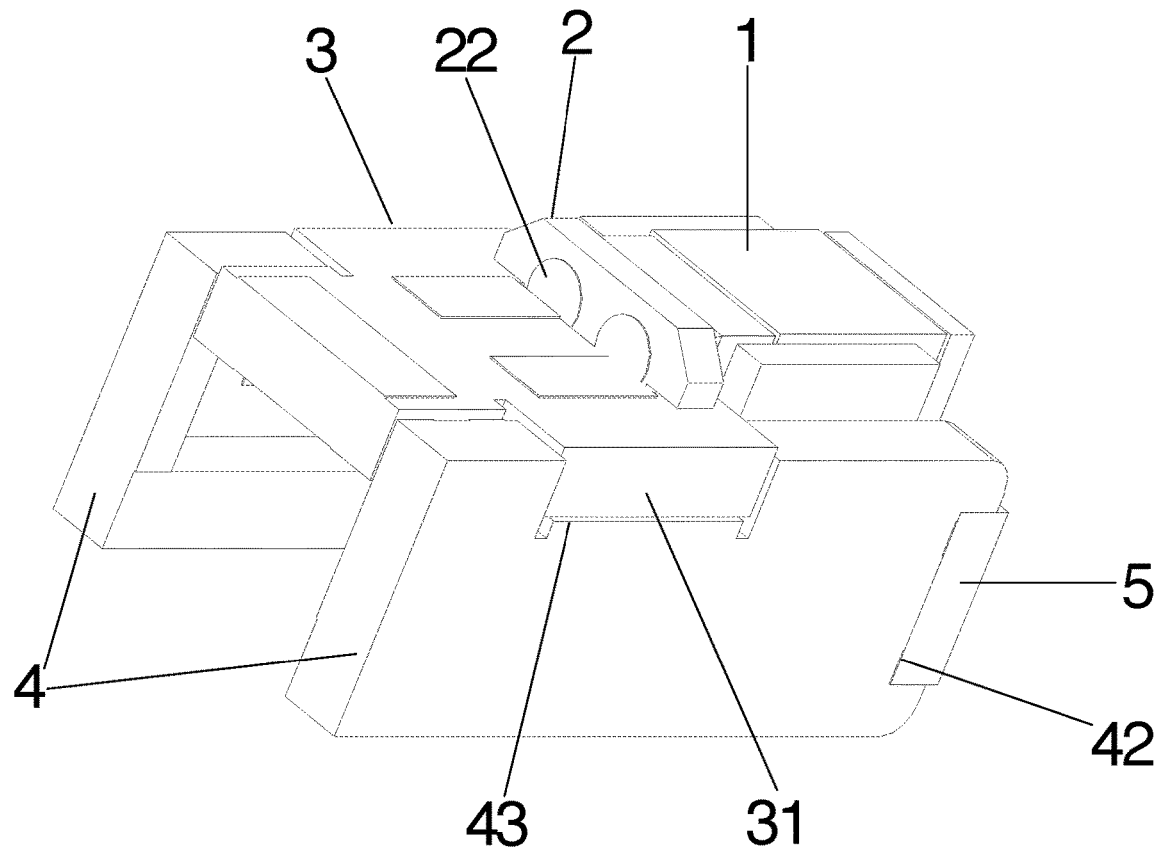
FIG. 4 is a schematic structural diagram 4 of an in-vivo detection apparatus based on a flexible tube according to an embodiment of the present invention.
Figure 5:
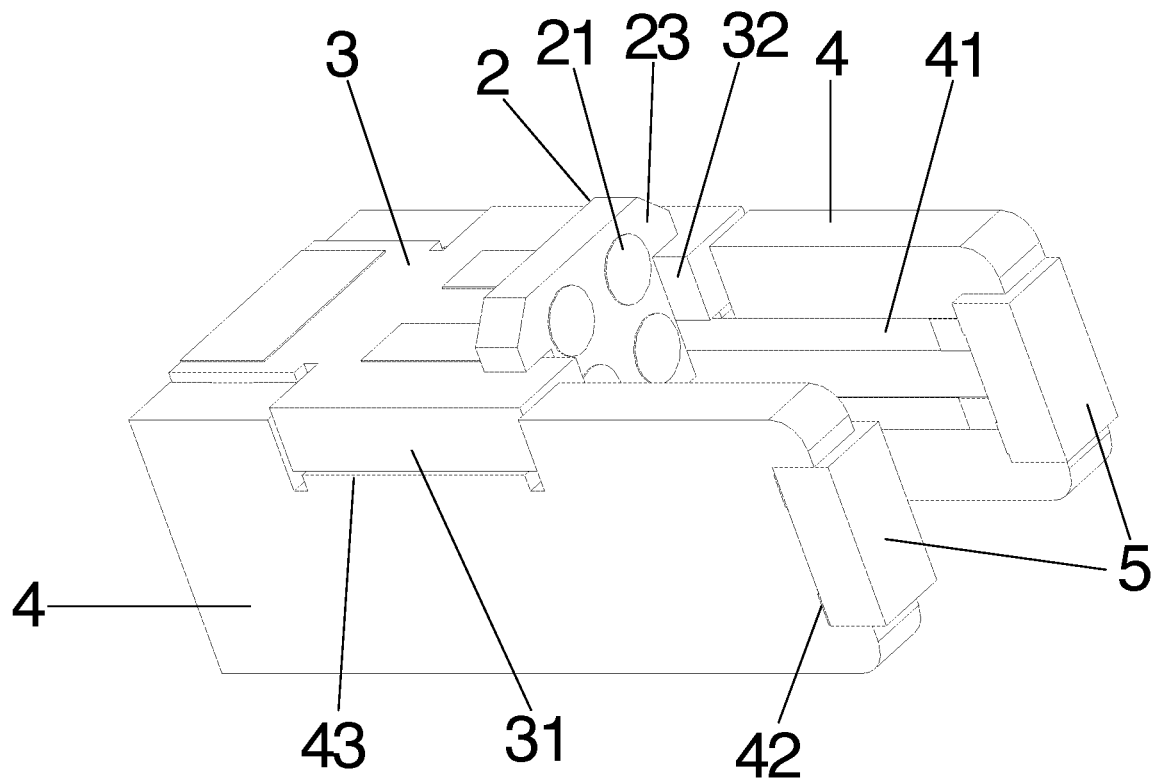
FIG. 5 is a schematic structural diagram 5 of an in-vivo detection apparatus based on a flexible tube according to an embodiment of the present invention.
Figure 6:
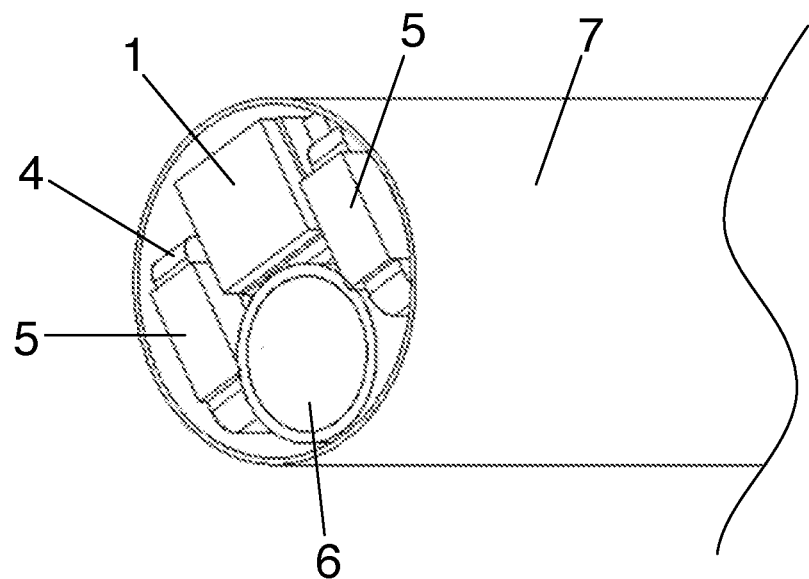
FIG. 6 is a schematic structural diagram 6 of an in-vivo detection apparatus based on a flexible tube according to an embodiment of the present invention.

FIG. 1 is a schematic structural diagram 1 of an in-vivo detection apparatus based on a flexible tube according to an embodiment of the present invention. FIG. 2 is a schematic structural diagram 2 of an in-vivo detection apparatus based on a flexible tube according to an embodiment of the present invention. FIG. 3 is a schematic structural diagram 3 of an in-vivo detection apparatus based on a flexible tube according to an embodiment of the present invention. FIG. 4 is a schematic structural diagram 4 of an in-vivo detection apparatus based on a flexible tube according to an embodiment of the present invention. FIG. 5 is a schematic structural diagram 5 of an in-vivo detection apparatus based on a flexible tube according to an embodiment of the present invention. FIG. 6 is a schematic structural diagram 6 of an in-vivo detection apparatus based on a flexible tube according to an embodiment of the present invention.

Referring to FIG. 1 to FIG. 6, the in-vivo detection apparatus based on the flexible tube includes: a detection component 1, a main circuit board 3, a detection circuit board 2, auxiliary circuit boards 4, a cable, and an outer tube 7.

The main circuit board 3 is provided with two first edges parallel to each other disposed along a first direction, and a second edge disposed along a second direction. It may be understood that the first edge is used to connect to an edge of the detection circuit board 2. It may be understood that the second edge is used to connect to an edge of the auxiliary circuit board 4.

A first conducting material 21 is disposed on a first side surface of the detection circuit board 2, the detection component 1 is connected to the first side surface of the detection circuit board 2, and a wiring terminal of the detection component 1 is welded to the first conducting material 21. A second conducting material 22 is disposed on a second side surface of the detection circuit board 2, the second side surface of the detection circuit board 2 is connected to the second edge of the main circuit board 3, the second conducting material 22 is perpendicularly welded to a conductive portion on a surface of the main circuit board 3, and the conductive portion is conductively connected to the cable. The first conducting material is conducted to the second conducting material.

The first conducting material 21 may be any material that can be connected and electrically conductive, and may be a metal sheet such as a copper sheet. In an implementation, the first conducting material may be disposed on the first side surface. In another optional implementation, the first conducting material 21 may also be disposed in an opening groove of the first side surface.

The second conducting material 22 can be any material that can be connected and electrically conductive, and may be a metal sheet such as a copper sheet. In an implementation, the second conducting material may be disposed on the second side surface. In another optional implementation, the second conducting material 22 may also be disposed in an opening groove of the second side surface.

In addition, the first conducting material 21 may be conductively connected to the second conducting material 22. The conduction and connection manner may be any manner in which two side surfaces of a circuit board are conducted and connected.

The conductive portion may include a line for power supply and may further include a line for signal transmission. Specifically, the conductive portion may include any conductive material, circuit, or the like, and may have a first connecting surface. The first connecting surface may be directly welded and connected to the second conducting material 22. The conductive portion may further have a second connecting surface. The first connecting surface and the second connecting surface may be integrated, and can conduct and transmit electrical signals. The second connecting surface can be welded and connected to a cable of a signal line, and a connection manner may be welding. The conductive portion may be any material that can be connected and electrically conductive, for example, a metal sheet such as a copper sheet. The metal sheet can be bent to form the first connecting surface and the second connecting surface. The conductive portion may be further conductively connected to the cable, the cable may be the signal line, or a part of the signal line for connection. In addition, a grounding portion may be further disposed on the main circuit board 3, and may also be conductively connected to a ground cable.

It may be seen that a conductive material of the detection circuit board 2 may be disposed to enlarge a welding spot of the detection component 1. The detection circuit board 2 is welded to the main circuit board 3, and the main circuit board 3 facilitates welding of the signal line, the conductive portion, and the like, and increases welding strength.

The first conducting material is welded to the wiring terminal of the detection component, and the first conducting material may form the connecting surface, thereby preventing the wiring terminal of the detection component from being welded to the cable. Because the wiring terminal needs to be welded only to the first conducting material on the first side surface, difficulty of welding operations is reduced, welding strength and reliability are enhanced, and welding stability in a plurality of motion statuses is satisfied.

In addition, the detection component 1 may be further connected to at least one of the detection circuit board 2 and the auxiliary circuit board 4 in any other manner. For example, in addition to welding of the first conducting material 21 and the cable, another surface of the detection component 1 may be welded to at least one of the detection circuit board 2 and the auxiliary circuit board 4.

In another optional implementation, a distance between the auxiliary circuit boards 4 may also be suitable for clamping the detection component 1 to locate positions of the auxiliary circuit boards. For example, the distance may be less than or equal to a maximum size of the detection component 1 along the second direction.

In this embodiment, each of the auxiliary circuit boards 4 is connected to one of the first edges, a channel for at least a part of the instrument tube 6 to pass through is formed between the two auxiliary circuit boards 4, and the channel is provided on a side, along a third direction, of the detection component 1, the main circuit board 3, and the detection circuit board 2.

The instrument tube 6 can be understood as a tube that can be equipped with a biopsy instrument, a laser instrument, or the like, and may be flexible. For details, refer to definitions of the instrument tube 6 in the controllable curved tube in the field for understanding.

The first direction, the second direction, and the third direction are perpendicular to each other. Specifically, all the main circuit board 3, the detection circuit board 2, and the auxiliary circuit board 4 are perpendicular to each other.

Stable mounting and use of the detection component 1 are ensured by using the main circuit board 3, the detection circuit board 2, and the auxiliary circuit board 4, so that the detection component 1 is not impacted by external force. In addition, the side surface of the auxiliary circuit board 4 is connected to the first edge of the main circuit board 3, the side surface of the detection circuit board 2 is connected to the second edge of the main circuit board 3, and the channel is formed to provide a cavity structure whose shape is similar to H, thereby avoiding an excessively large size in any direction, and helping reduce an overall size of the apparatus by rationalizing space utilization.

In an implementation, a surface size of the second conducting material 22 is greater than a surface size of the first conducting material 21. Therefore, because a surface size of the second conducting material 22 is greater than a surface size of the first conducting material 21, after the main circuit board 3 is perpendicularly welded to the second conducting material 22 of the detection circuit board 2, a connection between the detection component 1 and the cable may be changed from a point to a line, thereby effectively enhancing welding strength and reliability, and satisfying welding stability in a plurality of motion statuses.

In an implementation, the detection component 1 may be an image acquisition component. In another optional implementation, the detection component 1 may also be any detection apparatus that detects physical and chemical properties of a liquid, a gas, or a solid, such as a liquid detection component or a gas detection component.

The detection component 1 may be the image acquisition component. With quick development of image sensors, the smallest image sensor can now achieve 0.7*0.7 mm. Therefore, there is an urgent need for a packaging structure that can effectively control an external diameter and be safely and reliably packaged with lighting and low costs. However, the apparatus in this embodiment can exactly meet this demand.

To be suitable for implementing effective image acquisition, the apparatus further includes a lighting component 5, where the lighting component 5 is disposed at an end of the auxiliary circuit board 4, and the lighting component 5 and the detection component 1 face a same direction. That is, the lighting component 5 is configured to shine to a direction in which the image acquisition component performs acquisition. Because the lighting component 5 is disposed at an end of the auxiliary circuit board 4, the lighting components may be symmetrically disposed on two sides of the detection component 1, so as to help implement clear lighting.

The lighting component 5 may be any component that can emit light, and may be any component with any color or any lighting principle. For example, the lighting component 5 may be an LED. In a specific implementation process, the lighting component 5 may be monochromatic, multicolor, or allochroic.

It may be seen that this embodiment is designed ingeniously, makes rational utilization of space, and is simple, reliable, and easy to manufacture. In addition, this embodiment may also be manufactured using common standard parts with low costs. Therefore, based on this embodiment, a radial packaging size of the detection component and the lighting component can be effectively controlled. In a specific implementation process, an overall apparatus with a diameter of less than 3 mm can be obtained through packaging, thereby greatly expanding an application scope of the detection component of, for example, a micro sensor in this field.

In a specific implementation process, referring to FIG. 5, a light conducting material 41 is disposed on each of opposite side surfaces of the two auxiliary circuit boards 4, the light conducting material 41 is welded to a wiring terminal of the lighting component 5, and the two lighting components are connected in parallel by using the two light conducting materials. The wiring terminal may include a cable for power supply, a signal line for control, or the like. In an example, the light conducting material 41 may be welded to another conductive portion on a surface of the main circuit board 3, and the two lighting components 5 are connected in parallel. The conductive portion can be understood with reference to the conductive portion connecting the second conducting material and the cable. In addition, the two conductive portions may be interconnected or independent of each other. In another example, the light conducting material 41 may also be directly welded to the cable, and the two lighting components 5 are connected in parallel.

It may be seen that, in this implementation, mounting of the lighting component 5 and electrical transmission may be further implemented by using the auxiliary circuit board 4 and the light conducting material 41 on the auxiliary circuit board 4. In addition, stability of electrical transmission of the lighting component 5 may be further ensured, and size simplification is facilitated.

In addition, the lighting component 5 may be further connected to at least one of the detection circuit board 2 and the main circuit board 3 in any other manner. For example, in addition to that the light conducting material 41 is welded to the corresponding cable and line, another surface of the lighting component 5 may be further welded to at least one of the detection circuit board 2 and the main circuit board 3, to further ensure a connection effect.

In an implementation, a bayonet is provided along the first direction at an end of the auxiliary circuit board 4, and the lighting component 5 is disposed at the bayonet. The bayonet may be specifically a second bayonet 42 shown in FIG. 3, FIG. 4, and FIG. 5.

A connection between the bayonet and the lighting component 5 may be performed by matching a size of the bayonet and a size of the lighting component 5. The matching may mean that sizes of the bayonet and the lighting component are the same along the third direction, or that the size of the bayonet along the third direction is less than the size of the lighting component 5 along the third direction. In addition, another auxiliary connection structure may be further disposed.

In the embodiments shown in FIG. 1 to FIG. 6, the second bayonet 42 may be C-shaped, to surround three side surfaces of the lighting component 5, to implement two-sided clamping on the lighting component 5.

Figure 7:
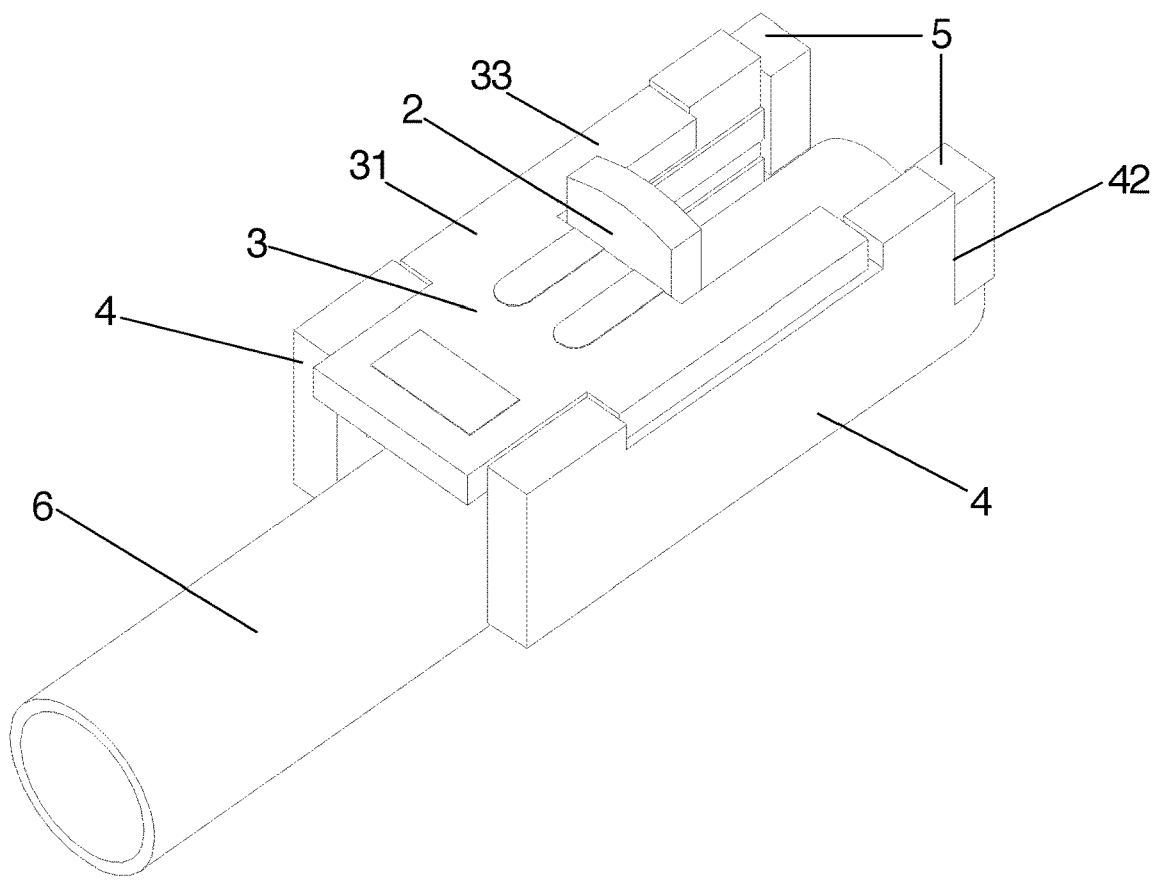
FIG. 7 is a schematic structural diagram 1 of an in-vivo detection apparatus based on a flexible tube according to another embodiment of the present invention.
Figure 8:
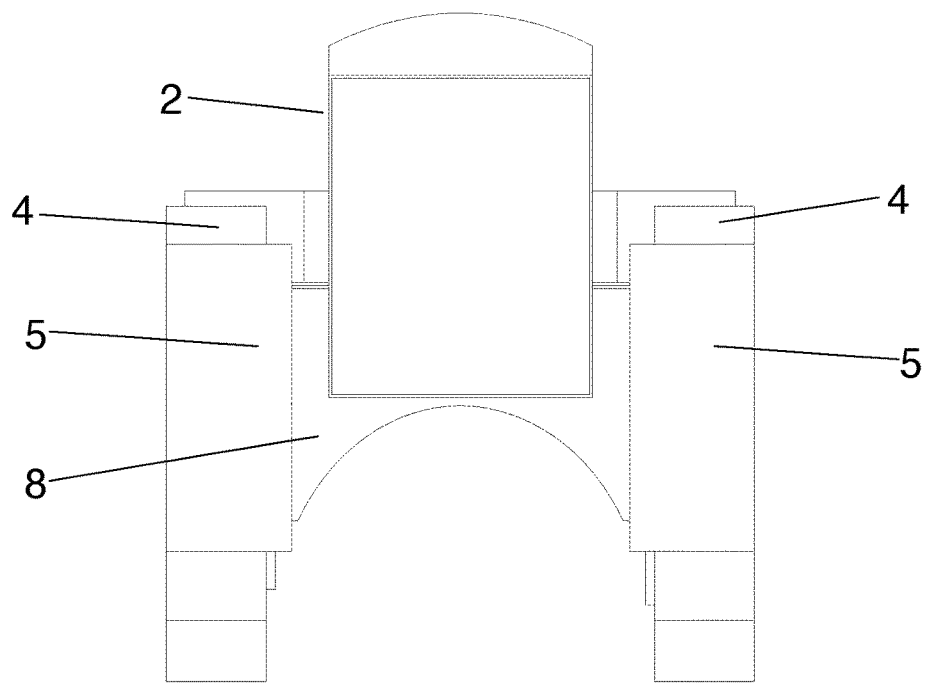
FIG. 8 is a schematic structural diagram 2 of an in-vivo detection apparatus based on a flexible tube according to another embodiment of the present invention, where

FIG. 7 is a schematic structural diagram 1 of an in-vivo detection apparatus based on a flexible tube according to another embodiment of the present invention. FIG. 8 is a schematic structural diagram 2 of an in-vivo detection apparatus based on a flexible tube according to another embodiment of the present invention.

In the embodiments shown in FIG. 7 and FIG. 8, the second bayonet 42 may be L-shaped, to surround two side surfaces of the lighting component 5, to implement single-sided clamping on the lighting component 5. The second bayonet 42 may facilitate mounting of the lighting component 5, especially facilitate mounting with a tolerance, and may also adapt to lighting components 5 of different sizes and models.

In an implementation, referring to FIG. 1 to FIG. 3, a distance between the lighting component 5 and the first side surface of the detection circuit board 2 along the first direction matches a length of the detection component 1 along the first direction. Therefore, it may be understood that the matching is performed, so that an end, distal from the detection circuit board 2, of the detection component 1 and an end, distal from the detection circuit board 2, of the lighting component 5 stay in a same reference plane, and the reference plane is a plane perpendicular to the first direction. In addition, the end of the lighting component 5 may also be slightly higher or lower than the end of the detection component 2 along the first direction. The two ends conform to the matching described above, and are also located in a same reference plane described above.

In the foregoing implementation, the lighting component 5 and the detection component 2 being in the same reference plane can make lighting more uniform.

In an implementation, the detection circuit board 2 and the main circuit board 3, and/or the auxiliary circuit board 4 and the main circuit board 3 are separately located and connected by using a locating bayonet structure.

Referring to FIG. 5, the locating bayonet structure of the detection circuit board 2 and the main circuit board 3 can be understood as including a first bayonet 32 located on the second edge of the main circuit board 3 and a first extension portion 23 extending on two sides of the detection circuit board 2 along the second direction. Therefore, a size of the first bayonet 32 matches the detection circuit board 2, so that when the detection circuit board 2 is embedded into the first bayonet 32, the first extension portion 23 may be erected on the main circuit board 3. In another optional implementation, referring to FIG. 7 and FIG. 8, the detection circuit board 2 may not have the first extension portion 23.

In a specific implementation, referring to FIG. 8, a support portion 8 is disposed on the detection circuit board 2 along the third direction on a side proximal to the channel. The support portion 8 may be connected to the detection circuit board 2. The detection circuit board 2 and the support portion may be integrated, or may be assembled together. Two sides of the support portion 8 along the second direction may be respectively connected to the two auxiliary circuit boards 4. In addition, a side, proximal to the channel, of the support portion 8 along the third direction may be an arc groove that matches an outer diameter of the instrument tube 6. The matching may mean that the arc groove is suitable for the instrument tube 6 to pass through. In addition, radiuses of curvature of the arc groove and the instrument tube may be the same or different. The support portion 8 may provide support between the two auxiliary circuit boards 4.

Referring to FIG. 3 to FIG. 5, a locating bayonet structure of the auxiliary circuit board 4 and the main circuit board 3 may be understood as including a second extension portion 31 extending on two sides of the main circuit board 3 along the second direction, and a third bayonet 43 provided on an edge of the auxiliary circuit board 4 along the third direction. The second extension portion 31 may be embedded into the third bayonet 43 corresponding to the auxiliary circuit board 4, so that the main circuit board 3 can be erected on the two auxiliary circuit boards 4.

In an implementation, referring to FIG. 7, for the second extension portion 31, a third extension portion 33 further extends along the first direction, and the third extension portion 33 may be disposed on two sides of the detection component 1 along the second direction. Correspondingly, a size of the third bayonet 43 may match a size of the second extension portion 31 and a size of the third extension portion 33, which may be understood as that the size of the third bayonet 43 along the first direction may be the same as or close to a sum of the size of the second extension portion 31 and the size of the third extension portion 33 along the first direction. The third extension portion 33 may help ensure stability of the structure.

Locating and a connection between circuit boards may be implemented based on the foregoing designs.

In an implementation, the cable conductively connected to the conductive portion is a coaxial cable with a shielding layer. The shielding layer can effectively increase welding strength and avoid occurrence of an abnormality in the cable.

Referring to FIG. 6, the detection component 1, the main circuit board 3, the detection circuit board 2, the auxiliary circuit board 4, and a part of the instrument tube 6 disposed in the channel are all disposed in the outer tube 7. The outer tube 7 can be filled with glue, through which locations of the circuit boards, components, and instrument tubes can be fixed, thereby implementing overall packaging of the apparatus.

It may be understood that, the outer tube 7 being filled with glue means that as long as there is glue in the outer tube 7, the above description applies regardless of whether all empty spaces are filled. In addition, even if only at least two of the detection component 1, the lighting component 5, the circuit boards, the instrument tube 6, and the outer tube 7 are connected by glue, the description of this embodiment also applies.

This embodiment further provides an in-vivo detection system based on a flexible tube, including the in-vivo detection apparatus based on the flexible tube, the flexible controllable curved tube, and the instrument tube in the foregoing embodiments and the optional manners of the foregoing embodiments, where the in-vivo detection apparatus and the instrument tube form an insertion portion at an end of the controllable curved tube.

The insertion portion and the controllable curved tube may be a controllable curved tube and an insertion portion of an endoscope.

To sum up, for the in-vivo detection apparatus and system based on the flexible tube provided in this embodiment, the first conducting material is disposed on the first side surface of the detection circuit board, and when the detection component is connected to the first side surface of the detection circuit board, the wiring terminal of the detection component is welded to the first conducting material, so that the wiring terminal of the detection component can be prevented from being welded to the cable. Because the wiring terminal needs to be welded only to the first conducting material on the first side surface, difficulty of welding operations is reduced, welding strength and reliability are enhanced, and welding stability in a plurality of motion statuses is satisfied.

Based on this embodiment, stable mounting and use of the detection component are further ensured by using the main circuit board, the detection circuit board, and the auxiliary circuit board, so that the detection component is not impacted by external force. In addition, the side surface of the auxiliary circuit board is connected to the first edge of the main circuit board, the side surface of the detection circuit board is connected to the second edge of the main circuit board, and the channel is formed to provide a cavity structure whose shape is similar to H, thereby helping reduce an overall size of the apparatus by rationalizing space utilization.

In an optional solution of the present invention, because a surface size of the second conducting material is greater than a surface size of the first conducting material, after the main circuit board is perpendicularly welded to the second conducting material of the detection circuit board, a connection between the detection component and the cable may be changed from a point to a line, thereby effectively enhancing welding strength and reliability, and satisfying welding stability in a plurality of motion statuses.

In an optional solution of this embodiment, mounting of the lighting component and electrical transmission may be further implemented by using the auxiliary circuit board and the light conducting material on the auxiliary circuit board. In addition, stability of electrical transmission of the lighting component may be further ensured, and size simplification is facilitated.

In an optional solution of this embodiment, a distance between the lighting component and the first side surface of the detection circuit board along the first direction matches a length of the detection component along the first direction, so that an end of the lighting component stays in a same plane as an end of the detection component, thereby ensuring lighting uniformity.

At last, it should be noted that the above various embodiments are only used to describe the technical solutions of the present invention, rather than limiting the technical solutions of the present invention. Even through the present invention is described in detail with reference to the foregoing embodiments, those of ordinary skilled in the art should understand that they can still modify the technical solutions recorded in the foregoing various embodiments or equivalently replace some or all of the technical features. However, these modifications or replacements do not make the essence of the corresponding technical solutions deviate from the scope of the technical solutions of the embodiments of the present invention.

What is claimed is:

1. An in-vivo detection apparatus based on a flexible tube, comprising:
   a detection component, a main circuit board, a detection circuit board, two auxiliary circuit boards, a cable, and an outer tube, wherein the main circuit board is provided with two first edges parallel to each other disposed along a first direction, and a second edge disposed along a second direction;
   a first conducting material is disposed on a first side surface of the detection circuit board, the detection component is connected to the first side surface of the detection circuit board, a wiring terminal of the detection component is welded to the first conducting material, a second conducting material is disposed on a second side surface of the detection circuit board, the second side surface of the detection circuit board is connected to the second edge of the main circuit board, the second conducting material is perpendicularly welded to a conductive portion on a surface of the main circuit board, and the conductive portion is conductively connected to the cable; the first conducting material is conducted to the second conducting material;
   each auxiliary circuit board is connected to one of the first edges, a channel for at least a part of an instrument tube to pass through is formed between two auxiliary circuit boards, and the channel is provided on a side, along a third direction, of the detection component, the main circuit board, and the detection circuit board;
   the detection component, the main circuit board, the detection circuit board, the auxiliary circuit boards, and the part of the instrument tube disposed in the channel are all disposed in the outer tube; the outer tube is directly or indirectly connected to a flexible controllable curved tube; and
   the first direction, the second direction, and the third direction are perpendicular to each other.

2. The in-vivo detection apparatus based on a flexible tube according to claim 1, wherein the detection component is an image acquisition component.

3. The in-vivo detection apparatus based on a flexible tube according to claim 2, further comprising a lighting component, wherein the lighting component is disposed at an end of the auxiliary circuit board, and the lighting component and the detection component face a same direction.

4. The in-vivo detection apparatus based on a flexible tube according to claim 3, wherein a light conducting material is disposed on each of opposite side surfaces of the two auxiliary circuit boards, the light conducting material is welded to a wiring terminal of the lighting component, and two lighting components are connected in parallel by using two light conducting materials.

5. The in-vivo detection apparatus based on a flexible tube according to claim 3, wherein a bayonet is provided along the first direction at an end of the auxiliary circuit board, and the lighting component is disposed at the bayonet.

6. The in-vivo detection apparatus based on a flexible tube according to claim 3, wherein a distance between the lighting component and the first side surface of the detection circuit board along the first direction matches a length of the detection component along the first direction.

7. The in-vivo detection apparatus based on a flexible tube according to claim 1, wherein a surface size of the second conducting material is greater than a surface size of the first conducting material.

8. The in-vivo detection apparatus based on a flexible tube according to claim 1, wherein the detection circuit board and the main circuit board, and/or the auxiliary circuit board and the main circuit board are separately located and connected by using a locating bayonet structure.

9. The in-vivo detection apparatus based on a flexible tube according to claim 1, wherein the cable conductively connected to the conductive portion is a coaxial cable with a shielding layer.

10. An in-vivo detection system based on a flexible tube, comprising the in-vivo detection apparatus based on the flexible tube according to claim 1; the flexible controllable tube; and the instrument tube, wherein the in-vivo detection apparatus and the instrument tube form an insertion portion at an end of the flexible controllable curved tube.

11. The in-vivo detection apparatus based on a flexible tube according to claim 2, wherein a surface size of the second conducting material is greater than a surface size of the first conducting material.

12. The in-vivo detection apparatus based on a flexible tube according to claim 3, wherein a surface size of the second conducting material is greater than a surface size of the first conducting material.

13. The in-vivo detection apparatus based on a flexible tube according to claim 4, wherein a surface size of the second conducting material is greater than a surface size of the first conducting material.

14. The in-vivo detection apparatus based on a flexible tube according to claim 5, wherein a surface size of the second conducting material is greater than a surface size of the first conducting material.

15. The in-vivo detection apparatus based on a flexible tube according to claim 6, wherein a surface size of the second conducting material is greater than a surface size of the first conducting material.

16. The in-vivo detection apparatus based on a flexible tube according to claim 2, wherein the detection circuit board and the main circuit board, and/or the auxiliary circuit board and the main circuit board are separately located and connected by using a locating bayonet structure.

17. The in-vivo detection apparatus based on a flexible tube according to claim 3, wherein the detection circuit board and the main circuit board, and/or the auxiliary circuit board and the main circuit board are separately located and connected by using a locating bayonet structure.

18. The in-vivo detection apparatus based on a flexible tube according to claim 4, wherein the detection circuit board and the main circuit board, and/or the auxiliary circuit board and the main circuit board are separately located and connected by using a locating bayonet structure.

19. The in-vivo detection apparatus based on a flexible tube according to claim 5, wherein the detection circuit board and the main circuit board, and/or the auxiliary circuit board and the main circuit board are separately located and connected by using a locating bayonet structure.

20. The in-vivo detection apparatus based on a flexible tube according to claim 6, wherein the detection circuit board and the main circuit board, and/or the auxiliary circuit board and the main circuit board are separately located and connected by using a locating bayonet structure.

21. The in-vivo detection system based on a flexible tube according to claim 10, wherein the detection circuit board and the main circuit board, and/or the auxiliary circuit board and the main circuit board are separately located and connected by using a locating bayonet structure.

22. The in-vivo detection system based on a flexible tube according to claim 11, wherein the detection circuit board and the main circuit board, and/or the auxiliary circuit board and the main circuit board are separately located and connected by using a locating bayonet structure.

23. The in-vivo detection system based on a flexible tube according to claim 12, wherein the detection circuit board and the main circuit board, and/or the auxiliary circuit board and the main circuit board are separately located and connected by using a locating bayonet structure.

24. The in-vivo detection system based on a flexible tube according to claim 13, wherein the detection circuit board and the main circuit board, and/or the auxiliary circuit board and the main circuit board are separately located and connected by using a locating bayonet structure.

25. The in-vivo detection system based on a flexible tube according to claim 14, wherein the detection circuit board and the main circuit board, and/or the auxiliary circuit board and the main circuit board are separately located and connected by using a locating bayonet structure.

26. The in-vivo detection system based on a flexible tube according to claim 10, wherein a surface size of the second conducting material is greater than a surface size of the first conducting material.

27. The in-vivo detection system based on a flexible tube according to claim 15, wherein the detection circuit board and the main circuit board, and/or the auxiliary circuit board and the main circuit board are separately located and connected by using a locating bayonet structure.

* * * * *